US00PP27519P2

(12) United States Plant Patent
Robb

(10) Patent No.: US PP27,519 P2
(45) Date of Patent: Dec. 27, 2016

(54) ***LAVANDULA* PLANT NAMED 'LMARO32-0'**

(50) Latin Name: *Lavandula stoechas*
Varietal Denomination: LMARO32-0

(71) Applicant: John Robb, Kariong (AU)

(72) Inventor: John Robb, Kariong (AU)

(73) Assignee: The Paradise Seed Company Pty Ltd (AU)

( * ) Notice: Subject to any disclaimer, the term of this patent is extended or adjusted under 35 U.S.C. 154(b) by 0 days.

(21) Appl. No.: 14/756,099

(22) Filed: Aug. 3, 2015

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — Cassandra Bright

(57) ABSTRACT

A new and distinct *Lavandula* cultivar named 'LMARO32-0' is disclosed, characterized by a long red-purple terminal bracts. Plants are typically upright in growth habit, strong and begin flowering early. The new variety is a *Lavandula*, normally produced as an outdoor garden or container plant.

2 Drawing Sheets

Figure 1:
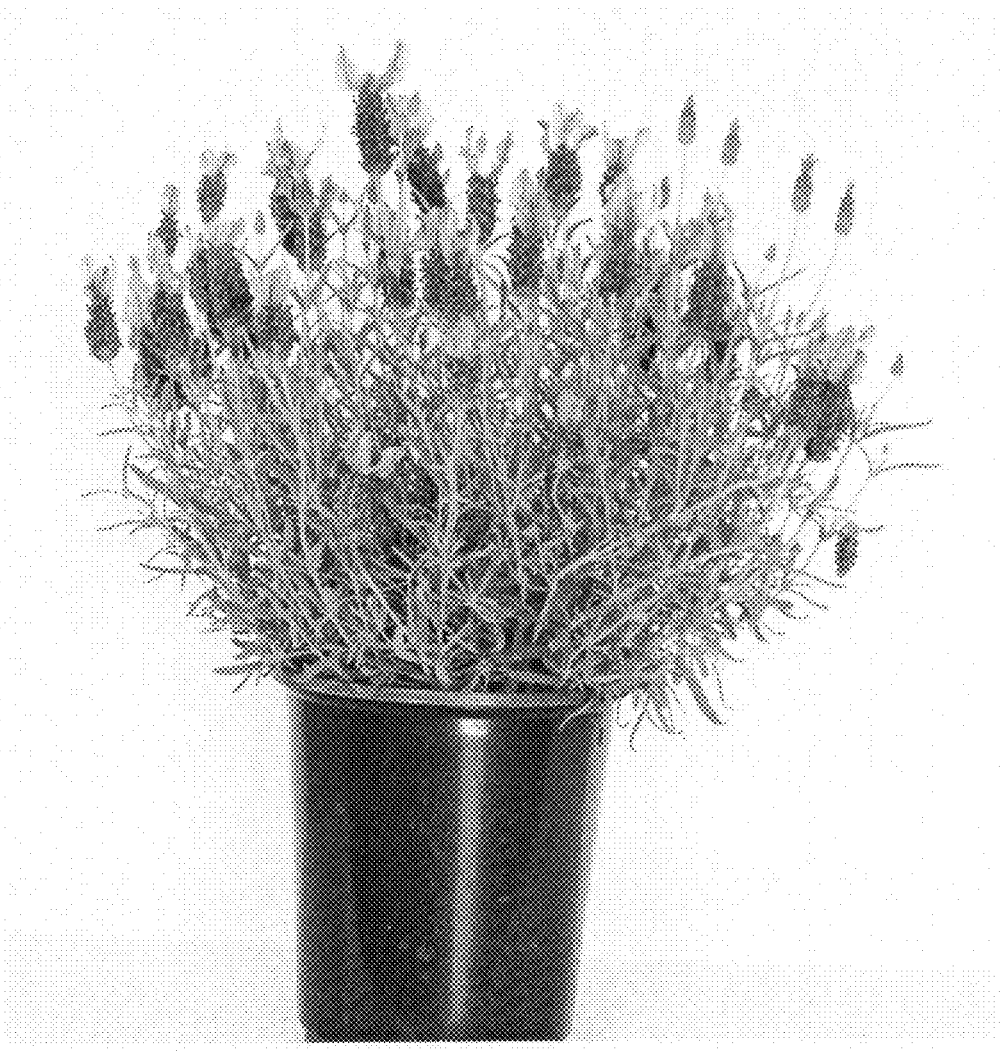

Latin name of the genus and species: *Lavandula stoechas*.
Variety denomination: 'LMARO32-0'.

BACKGROUND OF THE INVENTION

The new *Lavandula* cultivar is a product of a planned breeding program conducted by the inventor, John Robb, in New South Wales, Australia. The objective of the breeding program was to produce new Lavender varieties for ornamental commercial applications. The open pollination resulting in this new variety was made during October of 2009.

The seed parent is the, unpatented variety referred to as Lavender 'Bee Pretty'. The pollen parent is unknown as it was an open pollination breeding program, using several proprietary pollen parents. The new variety was discovered in October of 2011 by the inventor in a group of seedlings resulting from the 2009 crossing, in a research greenhouse in New South Wales, Australia.

Asexual reproduction of the new cultivar was performed by vegetative terminal cuttings. This was first performed at a research greenhouse in New South Wales, Australia during January of 2012 and has shown that the unique features of this cultivar are stable and reproduced true to type in at least 4 successive generations.

SUMMARY OF THE INVENTION

The cultivar 'LMARO32-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LMARO32-0' These characteristics in combination distinguish 'LMARO32-0' as a new and distinct Lavender cultivar:

1. Distinctive dark red-purple sterile bracts.
2. Upright growth habit.

3. Strong plants, resistant to breakage.
4. Good tolerance for heat and humidity.
5. Early flowering.

PARENT COMPARISON

Plants of the new cultivar 'LMARO32-0' are similar to plants of the parent, *Lavandula stoechas* 'Bee Pretty' in most horticultural characteristics, however, plants of the new cultivar 'LMARO32-0' produce flowers with darker sterile bracts. Additionally, plants of the new variety are more upright, and stronger. Foliage of the new variety is also a different shade of green than foliage of the seed parent.

COMMERCIAL COMPARISON

Plants of the new cultivar 'LMARO32-0' are comparable to the variety *Lavandula* 'Larkman Bee', U.S. Plant Pat. No. 20,840. The two *Lavandula* varieties are similar in most horticultural characteristics, including early flowering. The new variety 'LMARO32-0' differs in producing longer sterile bracts, of a red-purple, compared to purple color. Additionally plants of 'LMARO32-0' are more upright than plants of this comparator.

Plants of the new cultivar 'LMARO32-0' can also be compared to the commercial variety *Lavandula* 'Madrid Pink Improved' U.S. Plant Pat. No. 14,205. These varieties are similar in most horticultural characteristics however, the new variety 'LMARO32-0' differs in producing longer sterile bracts, and an overall longer inflorescence. Sterile bracts of the new variety fade to a lighter red-purple, whereas sterile bracts of the comparator fade to white. Additionally plants of 'LMARO32-0' are more upright in habit than the comparator.

BRIEF DESCRIPTION OF THE PHOTOGRAPHS

The accompanying photograph in FIG. 1 illustrates in full color a typical plant of 'LMARO32-0' grown outdoors in Santa Paula, Calif. The plant grown in a commercial 1 gallon container. Age of the plants photographed is approximately 30 weeks from a rooted cutting.

Figure 2:
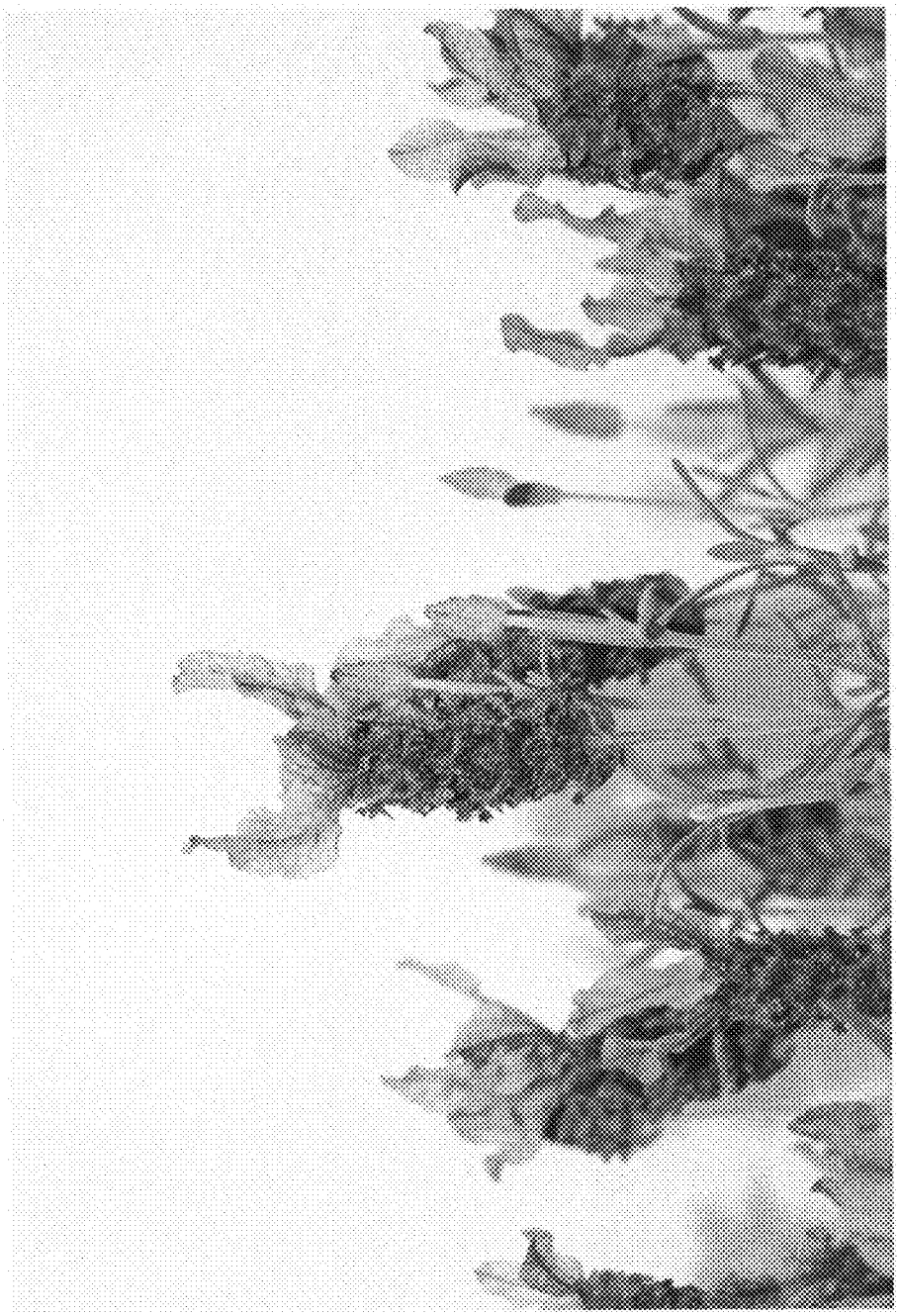

FIG. 2 illustrates a close up of the inflorescence. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LMARO32-0' plants grown outdoors during, Fall, Winter and Spring in Watsonville, Calif. The growing temperature ranged from 10° C. to 35° C. during the day and from 5° C. to 25° C. during the night. General light conditions are bright, normal sunlight. Measurements and numerical values represent averages of typical plant types.

Botanical classification: *Lavandula stoechas* 'LMARO32-0'.

PROPAGATION

Time to initiate roots: About 10 to 14 days at approximately 21° C.

Time to produce a rooted cutting: About 25 to 35 days at 21° C.

PLANT

Age of plant described: Approximately 9 months from an unrooted cutting.

Pot size: 1 Gallon

Plant spread: Approximately 35 cm.

Plant height: Approximately 30 cm, to top of flowering plane. Approximately 24 cm to top of foliar plane.

Growth rate: Moderate.

Length of primary lateral branches: Approximately 14 cm.

Diameter of lateral branches: Approximately 0.25 cm.

Quantity of lateral branches: About 30.

Plant habit: Moderately dense, upright, with a slight outward arch.

Stem:

- *Color*.—Near RHS Yellow-Green 144C and 144D.
- *Texture*.—Puberulent.

Internode length: Average range 1.5 to 3.0 cm.

FOLIAGE

Leaf:

- *Arrangement*.—2 large opposite leaves at each node.
- *Leaf type*.—Simple.
- *Quantity*.—Average 8 to 16 fully expanded per main branch.
- *Average length*.—Average 2.8 (mature foliage).
- *Average width*.—Average 0.4 cm. (mature foliage).
- *Shape of blade*.—Lanceolate.
- *Apex*.—Acute.
- *Base*.—Truncate.
- *Attachment*.—Sessile.
- *Margin*.—Entire.
- *Texture of all surfaces*.—Puberbulent.
- *Leaf fragrance*.—Less than moderate Lavender scent.
- *Color*.—Young foliage upper side: Near RHS Yellow-Green 144A. Young foliage under side: Near RHS Green Yellow-Green 144A. Mature foliage upper side: Near RHS Green 137A. Mature foliage under side: Near RHS Green 137C.
- *Venation*.—Type: Reticulate. Venation color upper side: Indistinguishable from foliage color. Venation color under side: Near RHS Green 138A.
- *Petiole*.—Absent.

FLOWER

Bloom period: Main flush during Spring. Lesser quantities of flowers produced throughout Summer and Fall. During peak flowering total inflorescence quantity between 50 and 60 per plant.

Inflorescence:

- *Form*.—Small single flower in verticillasters arranged in spikes. Typically 4 rows of flowers, occasionally up to 8 rows. Flowers have small bracts, and large showy terminal bracts.
- *Number of individual flowers per spike*.—Average 40.
- *Fragrance*.—Very strong lavender scent.
- *Inflorescence size, excluding terminal bracts*.—Length: Approximately 6.0 cm. Width: Approximately 1.8 cm. Shape: Cylindrical.

Flowers:

- *Corolla shape*.—Salverform.
- *Length*.—Average 1.0 cm.
- *Width*.—Average 0.5 cm.

Petals:

- *Petal number*.—5.
- *Petals fused or unfused*.—Fused at base.
- *Petal shape*.—Ovate.
- *Petal margin*.—Entire.
- *Petal surfaces*.—Glabrous. Length: Approximately 0.7 cm. (corolla tube and petals). Diameter: Approximately 0.2 cm at widest opening of petals.
- *Coloration of individual flowers, excluding terminal bracts*.—Immature: Near Red-Purple 70A. Mature: Near Red-Purple 61A. Fading: Near Purple 79A.

Sepals:

- *Calyx width*.—0.3 cm.
- *Calyx length*.—0.9 cm.
- *Calyx shape*.—Flattened tube.
- *Calyx color*.—RHS Yellow-Green 145D, heavily flushed Greyed-Purple N187A.

Bracts:

- *Bract shape*.—Orbicular.
- *Length*.—Approximately 0.7 cm.
- *Width*.—Approximately 0.6 cm.
- *Bract apex*.—Irregular apiculate.
- *Bract color*.—Lower Surface: Near Green 137C, flushing of veins near Purple N79A. Upper Surface: Near Green 137D.

Terminal bracts (sterile):

- *Quantity*.—4 per inflorescence, 2 large and 2 small.
- *Large bracts*.—Attitude and angle of attachment: Bracts arising at approximately 10 degree angle from the top of the inflorescence. Large Bracts: Length: Approximately 3.2 cm. Width: Approximately 1.3 cm. Small Bracts: Length: Approximately 2.0 cm. Width: Approximately 1.3 cm.
- *Form*.—Petaloid.
- *Margin*.—Entire and undulating, ruffled.

*Surfaces*.—Smooth.
*Appearance*.—Matte.
*Shape*.—Oblanceolate.
*Apex*.—Acute.
*Base*.—Oblique.
*Vein pattern*.—Reticulate.
*Duration on plant*.—Approximately 12 weeks, with good color. Persistent.
*Color*.—Lower Surface: Near Red-Purple 71C, veins near Greyed-Purple N187A. Upper Surface: Near Red-Purple 70B, veins near Purple N79A. Bract color fading to: Near RHS Red-Purple 70D, veins Yellow-Green 144A.

Peduncle:
*Peduncle length*.—Average range approximately 4.5 to 6.8 cm.
*Peduncle diameter*.—Approximately 0.2 cm.
*Texture*.—Pubescent.
*Aspect*.—Straight to slightly undulating.
*Color*.—Near RHS Yellow-Green 144D.

REPRODUCTIVE ORGANS

*Androecium*.—Stamens: 4. Anther shape: linear. Anther length: Approximately 0.5 mm. Anther color: Near RHS White N155A. Pollen quantity: Pollen production not observed.

*Pistil*.—Number: 1. Length: Approximately 0.25 cm. Style: Length: Approximately 0.2 cm. Color: Near RHS Yellow-Green 145D. Stigma: Shape: Linear. Color: Near RHS Greyed-Purple N187A. Ovary: Minute and immeasurable.

OTHER CHARACTERISTICS

Seeds and fruits: Seed production not observed to date.
Disease/pest resistance: Neither resistance nor susceptibility to the normal diseases and pests of *Lavandula stoechas*. has been observed. *Lavandula* is not affected by many diseases and pets. However, *Botrytis* and some root rot pathogens can be diseases problems, especially in overly wet conditions. Various species of White Fly may infect *Lavandula.*
Drought tolerance and cold tolerance: Hardy perennial. Tolerates high temperature to at least 32° C. Tolerates low temperatures to appoximately −12° C. While specific drought tolerance has not been observed, once plants are established very little water is necessary to maintain plants.
Fruit/seed production: Fruit and seed production not observed.

What is claimed is:

1. A new and distinct cultivar of *Lavandula* plant named 'LMARO32-0' as herein illustrated and described.

* * * * *